United States Patent [19]

Spindler et al.

[11] Patent Number: 5,563,308
[45] Date of Patent: * Oct. 8, 1996

[54] FERROCENE DIPHOSPHINES AS LIGANDS FOR HOMOGENEOUS CATALYSTS

[75] Inventors: Felix Spindler, Starrkirch-Wil, Switzerland; Amina Wirth-Tijani, Burnhaupt-le-Haut, France; Heidi Landert, Rheinfelden, Switzerland

[73] Assignee: Ciba-Geigy Corporation, Tarrytown, N.Y.

[ * ] Notice: The term of this patent shall not extend beyond the expiration date of Pat. No. 5,563,309.

[21] Appl. No.: 461,349

[22] Filed: Jun. 5, 1995

Related U.S. Application Data

[62] Division of Ser. No. 313,484, Sep. 27, 1994, Pat. No. 5,466,844, which is a continuation of Ser. No. 200,133, Feb. 22, 1994, abandoned.

[30] Foreign Application Priority Data

Feb. 26, 1993 [CH] Switzerland ............... 592/93

[51] Int. Cl.$^6$ ............... C07C 5/02; C07F 17/00
[52] U.S. Cl. ............... 585/277; 585/275; 556/14; 556/28; 556/136; 556/146; 526/943
[58] Field of Search ............... 585/275, 277; 556/14, 28, 136, 146

[56] References Cited

U.S. PATENT DOCUMENTS

| | | | |
|---|---|---|---|
| 4,994,615 | 2/1991 | Spindler | 564/304 |
| 5,011,995 | 4/1991 | Pilgin | 564/302 |
| 5,128,478 | 7/1992 | Ito | 548/237 |
| 5,371,256 | 12/1994 | Togni et al. | 556/14 |

FOREIGN PATENT DOCUMENTS 0564406 10/1993 European Pat. Off. .

OTHER PUBLICATIONS

Bull. Chem. Soc. Japan, 53, pp. 1136–1151 (1980).

*Primary Examiner*—Porfirio Nazario-Gonzales
*Attorney, Agent, or Firm*—Kevin T. Mansfield

[57] ABSTRACT

Compounds of formula I

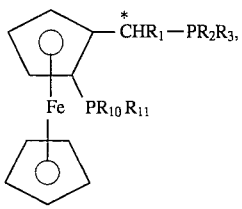

wherein $R_1$ is $C_1$–$C_8$alkyl, phenyl or phenyl which is substituted by 1 to 3 $C_1$–$C_4$alkyl or $C_1$–$C_4$alkoxy groups; $R_2$ and $R_3$ are each independently of the other typically $C_1$–$C_{12}$alkyl, $C_5$–$C_{12}$cycloalkyl, phenyl, or $C_1$–$C_4$alkyl- or $C_1$–$C_4$alkoxy-substituted $C_5$–$C_{12}$ cycloalkyl, or phenyl which is substituted by one to three identical or different members selected from the group consisting of $C_1$–$C_4$alkyl, $C_1$–$C_4$alkoxy or halogen;

$R_{10}$ and $R_{11}$ are identical and are typically $C_1$–$C_{12}$alkyl, $C_5$–$C_{12}$cycloalkyl, $C_1$–$C_4$alkyl- or $C_1$–$C_4$alkoxy-substituted $C_5$–$C_{12}$cycloalkyl or phenyl which is substituted by 1 to 3 identical or different members selected from the group consisting of $C_1$–$C_4$alkyl, $C_1$–$C_4$alkoxy or halogen; or $R_{10}$ and $R_{11}$ are different and are $C_1$–$C_{12}$alkyl, $C_5$–$C_{12}$cycloalkyl, $C_1$–$C_4$alkyl- or $C_1$–$C_4$alkoxy-substituted $C_5$–$C_{12}$cycloalkyl, phenyl or phenyl which is substituted by 1 to 3 identical or different members selected from the group consisting of $C_1$–$C_4$alkyl, $C_1$–$C_4$alkoxy or halogen, and * denotes a stereogenic carbon atom, in the form of their racemates and diastereoisomers or mixtures of diastereoisomers.

Rhodium and iridium complexes with these ligands are suitable for use as homogeneous enantioselective catalysts for the hydrogenation of prochiral compounds containing carbon double bonds or carbon/hetero atom double bonds.

6 Claims, No Drawings

FERROCENE DIPHOSPHINES AS LIGANDS FOR HOMOGENEOUS CATALYSTS

This is a division of Ser. No. 08/313,484, filed Sep. 27, 1994, U.S. Pat. No. 5,466,844, which is a continuation of Ser. No. 08/200,133, filed Feb. 22, 1994, now abandoned.

The present invention relates to 1-[2-(phosphino)ferrocenyl]alkylidene phosphines in the form of racemates and stereoisomers, to a process for their preparation, to iridium and rhodium complexes containing these ligands, and to the use thereof as enantioselective hydrogenation catalysts for the homogeneous hydrogenation of prochiral unsaturated compounds.

T. Hayashi et al. describe in Bull. Chem. Soc. Jpn., 53, pages 1136–1151, the preparation of a chiral ferrocenyl phosphine as ligand for transition metal complexes for asymmetric synthesis, namely [(R)-[(S)-2-(diphenylphosphino)ferrocenyl]ethyl]diphenylphosphine. Our investigations have revealed that homogeneous hydrogenations of prochiral compounds with rhodium complexes which contain these ligands give only low optical yields.

It has now been found that, if the reaction times are the same or even shorter, the enantio-selectivity can be substantially enhanced if the substituents in the 2-phosphino group are not both phenyl.

In one of its aspects, the invention relates to compounds of formula I

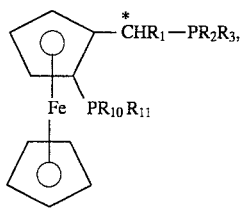

wherein $R_1$ is $C_1$–$C_8$alkyl, phenyl or phenyl which is substituted by 1 to 3 $C_1$–$C_4$alkyl or $C_1$–$C_4$alkoxy groups; $R_2$ and $R_3$ are each independently of the other $C_1$–$C_{12}$alkyl, $C_5$–$C_{12}$cycloalkyl, phenyl, $C_1$–$C_4$alkyl- or $C_1$–$C_4$alkoxy-substituted $C_5$–$C_{12}$cycloalkyl, or phenyl which is substituted by one to three identical or different members selected from the group consisting of $C_1$–$C_4$alkyl, $C_1$–$C_4$alkoxy, —$SiR_4R_5R_6$, halogen, —$SO_3M$, —$CO_2M$, —$PO_3M$, —$NR_7R_8$ and —$[^{\oplus}NR_7R_8R_9]X^{\ominus}$; or the group —$PR_2R_3$ is a radical of formula II

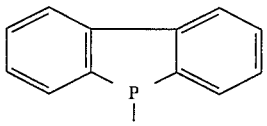

and $R_4$, $R_5$ and $R_6$ are each independently of one another $C_1$–$C_{12}$alkyl or phenyl, $R_7$ and $R_8$ are H, $C_1$–$C_{12}$alkyl, phenyl or $R_7$ and $R_8$, taken together, are tetramethylene, pentamethylene or 3-oxa-1,5-pentylene, $R_9$ is H or $C_1$–$C_4$alkyl, $R_{10}$ and $R_{11}$ are identical and are $C_1$–$C_{12}$alkyl, $C_5$–$C_{12}$cycloalkyl, $C_1$–$C_4$alkyl- or $C_1$–$C_4$alkoxy-substituted $C_5$–$C_{12}$cycloalkyl or phenyl which is substituted by 1 to 3 identical or different members selected from the group consisting of $C_1$–$C_4$alkyl, $C_1$–$C_4$alkoxy, —$SiR_4R_5R_6$, halogen, —$SO_3M$, —$CO_2M$, —$PO_3M$, —$NR_7R_8$ and —$[^{\oplus}NR_7R_8R_9]X^{\ominus}$; or $R_{10}$ and $R_{11}$ are different and are $C_1$–$C_{12}$alkyl, $C_5$–$C_{12}$cycloalkyl, $C_1$–$C_4$alkyl- or $C_1$–$C_4$alkoxy-substituted $C_5$–$C_{12}$cycloalkyl, phenyl or phenyl which is substituted by 1 to 3 identical or different members selected from the group consisting of $C_1$–$C_4$alkyl, $C_1$–$C_4$alkoxy, —$SiR_4R_5R_6$, halogen, —$SO_3M$, —$CO_2M$, —$PO_3M_2$, —$NR_7R_8$ and —$[^{\oplus}NR_7R_8R_9]X^{\ominus}$; or the group —$PR_{10}R_{11}$ is a radical of formula II

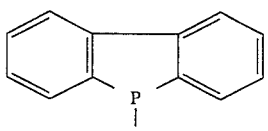

M is H or an alkali metal, $X^{\ominus}$ is the anion of a monobasic acid, and * is a stereogenic carbon atom, in the form of their racemates and diastereoisomers or mixtures of diastereoisomers.

$R_1$ defined as alkyl may be linear or branched and contains preferably 1 to 4 carbon atoms. Typical examples are methyl, ethyl, n- and isopropyl, n-, iso- and tert-butyl, pentyl, hexyl, heptyl and octyl. Methyl and ethyl are preferred and methyl is especially preferred.

$R_1$ defined as substituted phenyl preferably contains 1 or 2 substituents. Alkyl substituents may typically be methyl, ethyl, n- and isopropyl, n-, iso- and tert-butyl. Methyl and ethyl are preferred. Alkoxy substituents may be methoxy, ethoxy, n- and isopropoxy, n-, iso- and tert-butoxy. Methoxy and ethoxy are preferred. In a preferred group of compounds of formula I, $R_1$ is preferably phenyl or phenyl which is substituted by one or two $C_1$–$C_4$alkyl or $C_1$–$C_4$alkoxy groups.

$R_2$, $R_3$, $R_{10}$ and $R_{11}$ defined as alkyl may be linear or branched and contain preferably 1 to 8, most preferably 1 to 4, carbon atoms. Typical examples are methyl, ethyl, n- and isopropyl, n-, iso- and tert-butyl, pentyl, hexyl, heptyl, octyl nonyl, decyl, undecyl and dodecyl. Methyl, ethyl, n- and isopropyl, n-, iso- and tert-butyl are preferred. When $R_2$ and $R_3$ and/or $R_{10}$ and $R_{11}$ are identical and alkyl they are most preferably isopropyl or tert-butyl.

$R_2$, $R_3$, $R_{10}$ and $R_{11}$ defined as cycloalkyl preferably contain 5 to 8, most preferably 5 or 6, ring carbon atoms. Exemplary of cycloalkyl are cyclopentyl, cyclohexyl, cycloheptyl, cyclooctyl, cyclodecyl and cyclododecyl. Cyclopentyl and cyclohexyl are preferred and cyclohexyl is especially preferred.

Cycloalkyl may be substituted, conveniently by 1 to 3 alkyl or alkoxy groups. Examples of such groups have been indicated above. Methyl and ethyl are preferred, as are also methoxy and ethoxy. Substituted cycloalkyl is typically methyl- and methoxycyclopentyl and methyl- and methoxycyclohexyl.

$R_2$, $R_3$, $R_{10}$ and $R_{11}$ defined as substituted phenyl preferably contain 1 or 2 substituents. Where phenyl contains 2 or 3 substituents, these may be identical or different.

Examples of alkyl and alkoxy substituents have been indicated above. Preferred alkyl and alkoxy substituents of phenyl are methyl, ethyl as well as methoxy and ethoxy.

Halogen as a substituent of phenyl may preferably be selected from the group consisting of —F, —Cl and —Br.

$R_4$, $R_5$ and $R_6$ may be linear or branched alkyl that preferably contains 1 to 8 and, most preferably, 1 to 4, carbon atoms. Exemplary alkyl substituents have been indicated above. Preferably alkyl is methyl, ethyl, n-propyl, n-butyl and tert-butyl. The substituent —$SiR_4R_5R_6$ is most preferably trimethylsilyl.

Among the acid phenyl substituents —$SO_3M$, —$CO_2M$ and —$PO_3M$, the —$SO_3M$ group is preferred. M is preferably H, Li, Na and K.

$R_7$ and $R_8$ defined as alkyl preferably contain 1 to 6, most preferably 1 to 4, carbon atoms. Alkyl is preferably linear. Preferred examples are methyl, ethyl, n-propyl and n-butyl. $R_9$ defined as alkyl is preferably methyl.

$X^\ominus$ as anion of a monobasic acid is preferably $Cl^\ominus$, $Br^\ominus$ or the anion of a carboxylic acid, typically formate, acetate, trichloroacetate or trifluoroacetate.

Representative examples of substituted phenyl are 2-methylphen-1-yl, 3-methylphen-1-yl, 4-methylphen-1-yl, 2- or 4-ethylphen-1-yl, 2- or 4-isopropylphen-1-yl, 2- or 4-tert-butylphen-1-yl, 2-methoxyphen-1-yl, 3-methoxyphen-1-yl, 4-methoxyphen-1-yl, 2- or 4-ethoxyphen-1-yl, 4-trimethylsilylphen-1-yl, 2- or 4-fluorophen-1-yl, 2,4-difluorophen-1-yl, 2- or 4-chlorophen-1-yl, 2,4-dichlorophen-1-yl, 2,4-dimethylphen-1-yl, 3,5-dimethylphen-1-yl, 2-methoxy-4-methylphen-1-yl, 3,5-dimethyl-4-methoxyphen-1-yl, 3,5-dimethyl-4-(dimethylamino)phen-1-yl, 2- or 4-aminophen-1-yl, 2- or 4-methylaminophen-1-yl, 2- or 4-(dimethylamino)phen-1-yl, 2- or 4-$SO_3H$-phen-1-yl, 2- or 4-$SO_3Na$-phen-1-yl, 2- or 4-[$^\oplus NH_3 Cl^\ominus$]phen-1-yl, 3,4,5-trimethylphen-1-yl or 2,4,6-trimethylphen-1-yl.

$R_2$ and $R_3$ as identical substituents are preferably phenyl, cyclohexyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl and 3,5-dimethyl-4-methoxyphen-1-yl.

Where $R_2$ and $R_3$ are different substituents, $R_2$ is preferably phenyl and $R_3$ is preferably cyclohexyl, 2- or 4-methylphen-1-yl, 2- or 4-methoxyphen-1-yl, 4-(dimethylamino)phen-1-yl, 3,5-dimethyl-4-(dimethylamino)phen-1-yl, 3,5-dimethyl-4-methoxyphen-1-yl or 4-tert-butylphen-1-yl.

In a preferred embodiment of the invention, $R_2$ and $R_3$ are identical substituents and are cyclohexyl or phenyl.

In a particularly preferred embodiment of the invention, in formula I $R_1$ is methyl and $R_2$ and $R_3$ are each cyclohexyl or phenyl.

When $R_{10}$ and $R_{11}$ are identical they are preferably cyclohexyl, tert-butyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl and 3,5-dimethyl-4-methoxyphen-1-yl. Cyclohexyl, 4-methylphen-1-yl, 3,5-dimethylphen-1-yl and tert-butyl are especially preferred.

When $R_{10}$ and $R_{11}$ are different, $R_{10}$ is preferably phenyl and $R_{11}$ is preferably cyclohexyl, 2- or 4-methylphen-1-yl, 2- or 4-methoxyphen-1-yl, 4-(dimethylamino)phen-1-yl, 3,5-dimethyl-4-(dimethylamino)phen-1-yl, 3,5-dimethyl-4-methoxyphen-1-yl or 4-tert-butylphen-1-yl.

Particularly preferred compounds of formula I are typically:

{(S)-1-[(R)-2-(di-para-tolylphosphino)ferrocenyl]}ethyldicyclohexylphosphine,

{(R)-1-[(S)-2-(dicyclohexylphosphino)ferrocenyl]}ethyldicyclohexylphosphine,

{(R)-1-[(S)-2-(di-tert-butylphosphino)ferrocenyl]}ethyldiphenylphosphine,

{(R)-1-[(S)-2-(dicyclohexylphosphino)ferrocenyl]}ethyldiphenylphosphine and

{(R)-1-[(S)-2-(di-(3,5-dimethylphenyl)phosphino)ferrocenyl]}ethyl bis(3,5-dimethylphenyl)phosphine.

The compounds of formula I are prepared either by reacting a compound of formula III

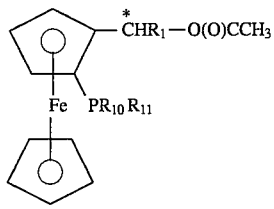

(III)

in the presence of an inert solvent, at room temperature or elevated temperature, with a phosphine of formula IV $HPR_2R_3$ (IV);

or reacting a compound of formula VII

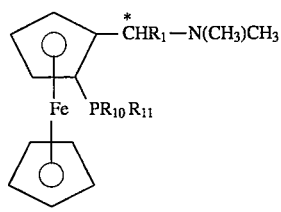

(VII)

wherein $R_1$, $R_{10}$ and $R_{11}$ are as defined for formula I, in the presence of an inert solvent, at room temperature or elevated temperature, with a phosphine of formula IV $HPR_2R_3$ (IV).

This process likewise constitutes a further object of the invention.

The reactions are known per se and are described by T. Hayashi et al. im Bull. Chem. Soc. Jpn., 53, pp. 1136–1151. The preparation of all stereoisomers of compounds of formulae III and VII is also described in this reference or can be carried out in analogous manner. The phosphines of formula IV are known or are obtainable by known methods in analogous manner.

The reaction temperature may be in the range from 20° to 150° C., preferably from 40° to 100° C. Suitable solvents are polar protic and aprotic solvents, which may be used singly or as mixtures of two or more solvents. Typical examples of solvents are alkanols such as methanol and ethanol, and carboxylic acids such as formic acid and acetic acid.

The compounds of formula I are obtained as racemates, mixtures of stereoisomers or as stereoisomers, depending on whether the compounds of formula III are used as racemates, mixtures of stereoisomers or as stereoisomers. Racemates and mixtures of stereoisomers can be separated by known methods into the stereoisomers, preferably as a rule by chromatographic methods.

The compounds of formula I are isolated and purified by per se known methods, typically by distillation, extraction, crystallisation and/or chromatographic methods.

The compounds of formula I are suitable for use as ligands for rhodium and iridium complexes. In another of its aspects, the invention relates to complexes of formulae V and VI $[X_1M_1YZ]$ (V)

$[X_1M_1Y]^\oplus A_1^\ominus$ (VI)

wherein $X_1$ is two $C_2$–$C_{12}$olefins or a $C_5$–$C_{12}$diene, Z is Cl, Br or I, $A_1^\ominus$ is the anion of an oxyacid or of a complex acid, $M_l$ is Rh or Ir, and Y is a diphosphine of formula I. The complexes of formula VI are preferred.

With respect to the diphosphines of formula I, the same preferences and exemplifications apply as stated previously.

$X_1$ as olefin preferably contains 2 to 6 and, most preferably, 2 to 4, carbon atoms. Ethylene is particularly preferred. Further examples are propene and 1-butene. $X_1$ as diene preferably contains 5 to 8 carbon atoms. The diene may be an open-chain or mono- or bicyclic diene. The two olefinic groups of the diene are preferably linked through one or two $CH_2$ groups. Typical examples are 1,3-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene, norbornadiene. $X_1$ is preferably two ethylene, 1,5-hexadiene, 1,5-cyclooctadiene or norbornadiene.

Z in formula V is preferably Cl or Br. Typical examples of $A_1^\ominus$ in formula VI are $ClO_4^\ominus$, $FSO_3^\ominus$, $CH_3SO_3^\ominus$, $CF_3SO_3^\ominus$, $BF_4^\ominus$, $PF_6^\ominus$, $SbCl_6^\ominus$, $AsF_6^\ominus$ and $SbF_6^\ominus$. Preferably $A_1$ is $^\ominus ClO_4^\ominus$, $CF_3SO_3^\ominus$, $BF_4^\ominus$, $PF_6^\ominus$ and $SbF_6^\ominus$.

The novel complexes are obtained in per se known manner by the reaction of equimolar amounts of a compound of formula I with a metal complex of formula $[M_1(X_1)Z]_2$ or $M_1(X_1)_2^\oplus A_1^\ominus$, wherein $M_1$, $X_1$, Z and $A_1^\ominus$ have the meanings previously assigned to them. The metal complexes are known, in which connection reference is made to, inter alia, EP-A-0 302 021 and U.S. Pat. No. 5,011,995.

The reaction is conveniently carded out under an inert gas atmosphere, typically argon, and expediently in the temperature range from 0° to 40° C., preferably at room temperature. The concurrent use of a solvent or mixture of solvents is advantageous, conveniently selected from the group consisting of hydrocarbons (benzene, toluene, xylene), halogenated hydrocarbons (methylene chloride, chloroform, chlorobenzene), alkanols (methanol, ethanol, 2-methoxyethanol), and ethers (diethyl ether, dibutyl ether, 1,2-dimethoxyethane, tetrahydrofuran, dioxane) or mixtures thereof. The novel complexes can be isolated and purified by conventional methods, or they can be prepared in situ prior to hydrogenation and then used in dissolved form direct as hydrogenation catalysts.

The novel complexes are preeminently suitable for use as homogeneous catalysts for the enantioselective hydrogenation of prochiral compounds containing carbon double bonds and carbon/hetero atom double bonds, typically compounds that contain a group selected from C=C, C=N, C=O, C=C—N and C=C—O [q.v. inter alia K. E. König, The Applicability of Asymmetric Homogeneous Catalysis, in James D. Morrison (ed.), Asymmetric Synthesis, Vol. 5, Academic Press, 1985]. Examples of such compounds are prochiral olefins, enamines, imines and ketones. Surprisingly high yields are obtained, normally even a quantitative chemical conversion, in short reaction times. Particularly surprising are the very high optical yields which are obtained with the novel complexes. The enantiomer excess (ee) may be more than 90%. It is possible to use racemates, mixtures of stereoisomers or stereoisomers of the complexes of formulae V and VI, mixtures of stereoisomers or stereoisomers being preferred.

In another of its aspects, the invention relates to the use of the novel complexes of formulae V and VI as homogeneous catalysts for the asymmetric hydrogenation of prochiral compounds containing carbon double bonds or carbon/hetero atom double bonds, especially those containing a C=C, C=N, C=O, C=C—N or C=C—O group. The preferred utility is for hydrogenating unsymmetric carbon double bonds, ketimines and ketones. The iridium complex of formulae V and VI is also preferred as catalyst for hydrogenating prochiral N-arylketimines to optically active secondary amines. The rhodium complex of formulae V and VI is preferably used as catalyst for hydrogenating carbon double bonds, for example prochiral carbon double bonds.

In yet another of its aspects, the invention provides a process for the asymmetric hydrogenation of prochiral compounds containing carbon double bonds or carbon/hetero atom double bonds under homogeneous reaction conditions, which process comprises hydrogenating said compounds in the temperature range from −20° to +80° C., and under a hydrogen pressure of $10^4$ to $10^7$ Pa, in the presence of a catalytic amount of a complex of formula V or VI.

Preferred prochiral compounds are those previously mentioned. Unsymmetric ketimines and ketones are known. Suitable N-arylketimines are disclosed, inter alia, in EP-A-0 256 982. N-Aliphatic ketimines are disclosed, inter alia, in EP-A-0 301 457. Such imines can be prepared from the corresponding unsymmetric ketones, which are known and commercially available or obtainable by known methods. Suitable substituted alkenes are described in the publication of K. E. König referred to above.

The process is preferably carried out in the temperature range from −10° to 50° C. and preferably under a hydrogen pressure of $1.10^5$ to $6.10^6$ Pa.

The amount of catalyst is preferably chosen such that the molar ratio of compound to be hydrogenated (substrate) to the complex of formula V or VI is preferably 10,000 to 20, more preferably 5000 to 20, especially 2000 to 40 and, most preferably, 1000 to 50.

A preferred mode of carrying out the process comprises the additional concurrent use of an ammonium or alkali metal chloride, bromide or iodide, especially when using the novel iridium catalysts. The amount may typically be 0.1 to 100, preferably 1 to 50 and, most preferably, 2 to 20, equivalents, based on the complex of formula V or VI. The addition of iodides is preferred. Ammonium is preferably tetraalkylammonium containing 1 to 6 carbon atoms in the alkyl groups, and the preferred alkali metal is lithium, sodium and potassium.

The hydrogenation can be carried out without, or in the presence of, a solvent. Suitable solvents, which may be used alone or in admixture, are typically: aliphatic and aromatic hydrocarbons (pentane, hexane, cyclohexane, methylcyclohexane, benzene, toluene, xylene), alcohols such as methanol, ethanol, propanol and butanol; ethers such as diethyl ether, 2-methoxyethyl ether, 1,2-dimethoxyethane, tetrahydrofuran and dioxane; halogenated hydrocarbons such as methylene chloride, chloroform, 1,1,2,2-tetrachloroethane and chlorobenzene; esters and lactones such as ethyl acetate, butyrolactone or valerolactone; carboxamides and lactams such as dimethyl formamide, dimethyl acetamide and N-methylpyrrolidone. Preferred mixtures are those of alcohols and aromatic hydrocarbons, typically methanol/benzene or methanol/toluene. The preferred solvent is methanol by itself or in admixture with benzene or toluene.

A particularly preferred embodiment of the novel process comprises hydrogenating a N-2,6-dialkylphen-4-ylketimine, typically N-2,6-dimethyl- or N-2-methyl-6-ethylphen-4-yl-methoxyacetonimine.

The novel hydrogenation process makes it possible to obtain optically pure compounds which are useful intermediates for the synthesis of biologically active compounds, especially in the pharmaceutical and agrochemical sectors. Thus, for example, herbicidally active 5-imidazolecarboxylic acid derivatives which can be used for weed control (EP-A-0 207 563) can be prepared from secondary amines, especially N-carbalkoxymethylamines. The optically pure α-aminocarboxylates are suitable for peptide syntheses.

Optically pure aminocarboxylic acids which are useful synthesis components can be obtained from unsaturated aminocarboxylic acids.

The following Examples illustrate the invention in more detail. The chemical conversion is determined by gas chromatography [column DB 17/30 W (15 m), supplier: JCW Scientific INC., USA, temperature program: 60/1 min up to 220° C., ΔT: 10° .min⁻1]. The determination of the optical yield, enantiomer excess ee) is likewise made by gas chromatography [column Chirasil-Val, 50 m, supplier: Alltech, USA, T: 150° C., isotherm), by HPLC (column Chiracel OD) or by $^1$H-NMR spectroscopy using shift reagents.

A) WORKING EXAMPLES

Example A 1

{(S)-1-[(R)-2-(di-p-tolylphosphino)ferrocenyl]}ethyl dicyclohexylphosphine (A).

1.2 g (2.56 mmol) of N-{[(S)-1-[(R)-2-(di-p-tolylphosphino)ferrocenyl]} ethyl dimethylamine (prepared from N-[(S)-1-ferrocenyl]ethyl dimethylamine and di-para-tolylphosphine chloride in accordance with Bull. Chem. Soc. Jpn., 53, 1138 (1980)], 15 ml of acetic acid and 0.62 ml (3.07 mmol) of dicyclohexylphosphine are charged in succession to a 25 ml Schlenk flask under argon and then heated, with stirring, for 25 minutes at 100° C. The crude product is then extracted from water/toluene. The organic phase is dried over sodium sulfate and the solvent is removed on a rotary evaporator. The residue is chromatographed over silica gel (solvent: diethyl ether). Recrystallisation of the crude product from hot ethanol gives 1.4 g of A (yield: 80%) as an orange crystalline substance; $[\alpha]^{22}_D$:+ 342° (c=0.41, CHCl$_3$); $^{31}$P-NMR (CDCl$_3$): 15.5 (d,J=27), −27.8 (d,J=27).

Example A2

{(R)-1-[(S)-2-(dicyclohexylphosphino)ferrocenyl]}ethyl dicyclohexylphosphine (B).

The general procedure of Example A1 is repeated, but using 0.262 g (0.579 mmol) of N-{(R)-1-[(S)-2-(dicyclohexylphosphino)ferrocenyl]}ethyl dimethylamine, 4 ml of acetic acid and 0.14 ml (0.695 mmol) of dicyclohexylphosphine, to give 0.23 g of B (yield 67%) as an orange crystalline substance; $^{31}$P-NMR (CDCl$_3$): 12.6 (d,J=6), −12.7 (d,J=6).

Example A3

{(R)-1-[(S)-2-(di-tert-butylphosphino)ferrocenyl]}ethyl diphenylphosphine (C).

The general procedure of Example A1 is repeated, but using 0.546 g (1.36 mmol) of N-{(R)-1-[(S)-2-(di-tert-butylphosphino)ferrocenyl]}ethyl dimethylamine, 5 ml of acetic acid and 0.28 ml (1.63 mmol) of diphenylphosphine, to give 0.37 g of C (yield: 50% ) as an orange crystalline substance; $^{31}$P-NMR (CDCl$_3$): 13.5 (d,J=10), −1.5 (d,J=10).

Example A4

{(R)-1-[(S)-2-(dicyclohexylphosphino)ferrocenyl]}ethyl diphenylphosphine (D).

The general procedure of Example A1 is repeated, but using 0.24 g (0.53 mmol) of N-{(R)-1-[(S)-2-(dicyclohexylphosphino)ferrocenyl]}ethyl dimethylamine, 4 ml of acetic acid and 0.11 ml (0.64 mmol) of diphenylphosphine, to give 0.12 g of D (yield: 38%) as an orange crystalline substance; $^{31}$P-NMR (CDCl$_3$): 4.6 (d,J=6), −−13.4 (d,J=6).

Example A5

{(R)-1-[(S)-2-(bis(3,5-dimethylphenyl)phosphino)ferrocenyl]}ethyl di(3,5-dimethylphenyl)phosphine (E).

The general procedure of Example A1 is repeated, with the following modifications to the reaction conditions:

1.0 g (2.0 mmol) of {(R)-1-[(S)-2-(bis(3,5-dimethylphenyl)phosphino)ferrocenyl]}ethyl dimethylamine, 0.53 g (2.2 mmol) of bis(3,5-dimethylphenyl)phosphine and 26 ml of acetic acid. The yield is 0.69 mg of E (49%) as an orange crystalline substance; $^{31}$P-NMR (CDCl$_3$): 7.9 (d,J=20), −24.7 (d,J=20).

Example A6

{(R)-1-[(S)-2-(dicyclohexylphosphino)ferrocenyl]}ethyl di-tert-butylphosphine (F).

The general procedure of Example A1 is repeated, with the following modifications to the reaction conditions:

0.91 g (2.0 mmol) of {(R)-1-[(S)-2-(dicyclohexyl)phosphino)ferrocenyl]}ethyl dimethylamine, 0.34 g (2.3 mmol) of di-tert-butylphosphine and 12 ml of acetic acid. The yield is 330 mg of F (30%) as an orange foamed substance; $^{31}$P-NMR (CDCl$_3$): 46.6 (d, J=16), −15.4 (d,J=16).

Example A7

{(R)-1-[(S)-2-(bis(2-naphthyl)phosphino)ferrocenyl]}ethyl diphenylphosphine (G).

The general procedure of Example A1 is repeated, with the following modifications to the reaction conditions:

380 mg g (0.7 mmol) of {(R)-1-[(S)-2-(bis(2-naphthyl)phosphino)ferrocenyl]}ethyl dimethylamine, 134 μl (0.77 mmol) of diphenylphosphine and 6 ml of acetic acid. The yield is 203 mg of G (42.5%) as an orange crystalline substance; $^{31}$P-NMR (CDCl$_3$): 7.0 (d, J=22), −23.3 (d,J=22).

Example A8

{(R)-1-[(S)-2-(bis(3,5-dimethylphenyl)phosphino)ferrocenyl]}ethyl diphenylphosphine (H).

The general procedure of Example A1 is repeated, with the following modifications to the reaction conditions:

1.0 g (2.0 mmol) of {(R)-1-[(S)-2-(bis(3,5-dimethylphenyl)phosphino)ferrocenyl]}ethyl dimethylamine, 0.4 ml (2.3 mmol) of diphenylphosphine and 15 ml of acetic acid. The yield is 804 mg of H (63%) as an orange crystalline substance; $^{31}$P-NMR (CDCl$_3$): 5.8 (d, J=20), −25.3 (d,J=20).

Example A9

{(R)-1-[(S)-2-(bis(2-naphthyl)phosphino)ferrocenyl]}ethyl bis(3,5-dimethylphenyl)phosphine (I).

The general procedure of Example A1 is repeated, with the following modifications to the reaction conditions:

1.08 g (2.0 mmol) of {(R)-1-[(S)-2-(bis(2-naphthyl)phosphino)ferrocenyl]}ethyl dimethylamine, 0.53 g (2.2 mmol) of bis(3,5-dimethylphenyl)phosphine and 15 ml of acetic acid. The yield is 1.07 g of I (72.3%) as an orange crystalline substance; $^{31}$P-NMR (CDCl$_3$): 8.1 (d,J=20), −23.9 (d,J=20).

B) Use Examples

Example B1

Preparation of N-acetylalinine methyl ester

A catalyst solution (prepared under argon) consisting of 12.8 mg (0.034 mmol) of [Rh(norbornadiene)$_2$]BF$_4$, 22.6 mg (0.036 mmol) of A and 5 ml of methanol is transferred by a steel capillary to a 200 ml glass reactor under argon. A solution of 750 mg (3.42 mmol) of Z-methyl-2-acetamidocinnamate (substrate) and 5 ml of methanol are then added in analagous manner. The molar ratio of substrate/catalyst is 100. Then hydrogenation is carried out with hydrogen in three cycles under a pressure of 0.1 MPa and the hydrogen pressure is set to 0.108 MPa. The reaction mixture is stirred for 30 minutes at 25° C. and then transferred to a flask and the solvent is stripped off on a rotary evaporator. The chemical conversion is 100%, and the N-acetylalinine methyl ester is obtained in an entiomer excess (ee) of 91.4% (S).

Example B2

Preparation of N-acetylalanine methyl ester

The general procedure described in Example B1 is repeated, with the following modifications to the reaction conditions: 21.7 mg (0.036 mmol) of B. The conversion is 100%, ee: 75% (R).

Example B3

Preparation of N-(2'-methyl-6-ethylphen-1'-yl)-N-(1-methoxymethyl)ethylamine 5 ml (24 mmol) of (2'-methyl-6-ethylphen-1'-yl)-N-(1-methoxymethyl)eth-1-ylideneamine, 10.2 mg (0.015 mmol) of [Ir(1,5-cyclooctadiene)Cl]$_2$, 23.2 mg (0.033 mmol) of E and 50 mg of tetrabutylammonium iodide are charged in succession to a 50 ml steel autoclave. The ratio of imine/catalyst is 800. The autoclave is closed and thereafter placed under gas (argon), which is introduced in three cycles. Then 20 ml of isopropanol are transferred to the autoclave by a steel capillary, with the exclusion of air. In three further cycles (2 MPa, normal pressure) the argon is expelled with hydrogen. The hydrogen is introduced under a pressure of 2.5 MPa. The reaction is discontinued after a reaction time of 18 hours at room temperature. The conversion is 100%, and the enantiomer purity is 81.6% (S).

Example B4

Preparation of N-(2'-methyl-6-ethylphen-1'-yl)-N-(1-methoxymethyl)ethylamine

The general procedure described in Example B3 is repeated, with the following modifications to the reaction conditions: G 22.8 mg (0.033 mmol), reaction time 18 hours. The conversion is 62%, ee: 75% (S).

Example B5

Preparation of N-(2'-methyl-6-ethylphen-1'-yl)-N-(1-methoxymethyl)ethylamine

The general procedure described in Example B3 is repeated, with the following modifications to the reaction conditions: I 24.6 mg (0.033 mmol), reactions time 18 hours. The conversion is 77%, ee: 80.4% (S).

Example B6

Preparation of methyl-3-hydroxybutyrate

All manipulations are carded out under an argon atmosphere. To a solution of 5.1 mg (0.011 mmol) of [Rh(norbornadiene)Cl]$_2$ in 10 ml of methanol are added 14.4 mg (0.023 mmol) of B. Separately, 0.51 g (4.4 mmol) of methyl acetoacetate in 5 ml of methanol. The substrate and the catalyst solution are added in succession by a steel capillary to a 50 ml steel autoclave under argon. The inert gas is expelled by hydrogen in three cycles (2 MPa, normal pressure). Then hydrogen is introduced under a pressure of 2.5 MPa. The reaction is discontinued after a reaction time of 20 hours at room temperature. The conversion is 100%, and the enantiomer purity is 94.5% (S).

Example 7

Preparation of methyl-3-hydroxybutyrate

The general procedure described in Example B6 is repeated, with the following modifications to the reaction conditions:

14.9 mg (0.024 mmol) of A. After a reaction time of 24 hours the conversion is 100%, and the enantiomer purity is 84.4% (S).

Example B8

Preparation of methyl mandelate

The general procedure described in Example B6 is repeated, with the following modifications to the reaction conditions:

0.268 g (1.63 mmol) of methyl phenyl glyoxylate, 3.9 mg (0.0084 mmol) of [Rh(norbornadiene)Cl]$_2$, 9.4 mg (0.018 mmol) of C, 10 ml of methanol. The hydrogen partial pressure is 4 MPa, the reaction temperature is 25° C. After a reaction time of 21 hours the conversion is 74%, and the optical yield is 52%.

Example B9

Preparation of N-acetylalanine methyl ester

The general procedure described in Example B6 is repeated, with the following modifications to the reaction conditions:

0[Rh(norbornadiene)$_2$]BF$_4$ 6.4 mg (0.017 mmol), E 13.1 mg (0.019 mmol), Z-methyl-2-acetamidocinnamate (substrate) 0.75 g (3.42 mmol), methanol 15 ml, hydrogen partial pressure 2 MPa, temperature 40° C., reaction time 2 hours. The conversion is 100%, ee 70% (S).

What is claimed is:

1. A process for the asymmetric hydrogenation of compounds containing carbon double bonds or carbon/hetero atom double bonds selected from C=N, C=O, C=C—N and C=C—O groups under homogeneous reaction conditions, which comprises hydrogenating said compounds in the temperature range from −20° to +80° C. and under a hydrogen pressure of $10^4$ to $10^7$ Pa in the presence of a catalytic amount of a complex of the formula V or VI

[X$_1$M$_1$YZ]  (V)

[X$_1$M$_1$Y]$^⊕$A$_1$$^⊖$  (VI)

wherein

X$_1$ is two C$_2$–C$_{12}$olefins or a C$_5$–C$_{12}$diene,

Z is Cl, Br or I, A$_1$$^⊖$ is the anion of an oxyacid or a complex acid,

M$_1$ is Rh or Ir, and Y is a compound of the formula I

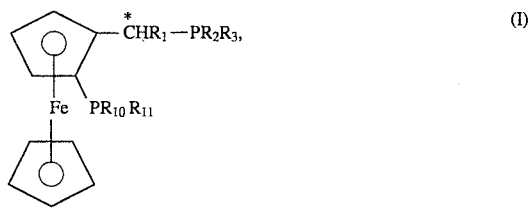

wherein

R$_1$ is C$_1$–C$_8$alkyl, phenyl or phenyl which is substituted by 1 to 3 C$_1$–C$_4$alkyl or C$_1$–C$_4$alkoxy groups;

R$_2$ and R$_3$ are each independently of the other C$_1$–C$_{12}$alkyl, C$_5$–C$_{12}$cycloalkyl, phenyl, C$_1$–C$_4$alkyl- or C$_1$–C$_4$alkoxy-substituted C$_5$–C$_{12}$cycloalkyl, or phenyl which is substituted by one to three identical or different members selected from the group consisting of C$_1$–C$_4$alkyl, C$_1$–C$_4$alkoxy, —SiR$_4$R$_5$R$_6$, halogen, —SO$_3$M, —CO$_2$M, —PO$_3$M, —NR$_7$R$_8$ and —[$^\oplus$NR$_7$R$_8$R$_9$]X$^\ominus$; or the group —PR$_2$R$_3$ is a radical of the formula II

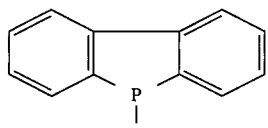

and

R$_4$, R$_5$ and R$_6$ are each independently of one another C$_1$–C$_{12}$alkyl or phenyl, R$_7$ and R$_8$ are H, C$_1$–C$_{12}$alkyl, phenyl or R$_7$ and R$_8$, taken together, are tetramethylene, pentamethylene or 3-oxa-1,5-pentylene, R$_9$ is H or C$_1$–C$_4$alkyl, R$_{10}$ and R$_{11}$ are identical and are C$_1$–C$_{12}$alkyl, C$_5$–C$_{12}$cycloalkyl, C$_1$–C$_4$alkyl- or C$_1$–C$_4$alkoxy-substituted C$_5$–C$_{12}$cycloalkyl or phenyl which is substituted by 1 to 3 identical or different members selected from the group consisting of C$_1$–C$_4$alkyl, C$_1$–C$_4$alkoxy, —SiR$_4$R$_5$R$_6$, halogen, —SO$_3$M, —CO$_2$M, —PO$_3$M, —NR$_7$R$_8$ or —[$^\oplus$NR$_7$R$_8$R$_9$]X$^\ominus$; or R$_{10}$ and R$_{11}$ are different and are C$_1$–C$_{12}$alkyl, C$_5$–C$_{12}$cycloalkyl, C$_1$–C$_4$alkyl- or C$_1$–C$_4$ alkoxy-substituted C$_5$–C$_{12}$cycloalkyl, phenyl or phenyl which is substituted by 1 to 3 identical or different members selected from the group consisting of C$_1$–C$_4$alkyl, C$_1$–C$_4$alkoxy, —SiR$_4$R$_5$R$_6$, halogen, —SO$_3$M, —CO$_2$M, —PO$_3$M$_2$, —NR$_7$R$_8$ or —[$^\oplus$NR$_7$R$_8$R$_9$]X$^\ominus$; or the group —PR$_{10}$R$_{11}$ is a radical of the formula II

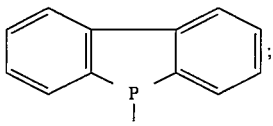

M is H or an alkali metal, X$^\ominus$ is the anion of a monobasic acid, and * is a stereogenic carbon atom, in the form of the racemates or diastereoisomers thereof or of a mixture of diastereoisomers.

2. A process according to claim 1, wherein the hydrogen pressure is from 10$^5$ to 6.10$^6$ Pa.

3. A process according to claim 1, wherein the temperature is in the range from −10° to +50° C.

4. A process according to claim 1, wherein the amount of catalyst is chosen such that the molar ratio of compound to be hydrogenated (substrate) to complex of formula V or VI is 10,000 to 20.

5. A process according to claim 1, wherein the reaction is carried out in the presence of a solvent.

6. A process according to claim 1, wherein the solvent is methanol or a mixture of methanol and benzene or toluene.

* * * * *